(12) United States Patent
Hui et al.

(10) Patent No.: US 6,964,778 B1
(45) Date of Patent: Nov. 15, 2005

(54) TEMPERATURE CONTROLLED CONTENT RELEASE FROM LIPOSOMES

(75) Inventors: Sek Wen Hui, Williamsville, NY (US); Arindam Sen, Williamsville, NY (US)

(73) Assignee: Health Research, Inc., Buffalo, NY (US)

( * ) Notice: Subject to any disclaimer, the term of this patent is extended or adjusted under 35 U.S.C. 154(b) by 242 days.

(21) Appl. No.: 10/236,546

(22) Filed: Sep. 6, 2002

(51) Int. Cl.$^7$ ............................................. A61K 9/127
(52) U.S. Cl. ..................................................... 424/450
(58) Field of Search .............................. 424/450, 1.21, 424/9.321, 9.51, 417; 428/402.2

(56) References Cited

U.S. PATENT DOCUMENTS

| | | | | |
|---|---|---|---|---|
| 5,364,632 A | * | 11/1994 | Benita et al. ................ | 424/450 |
| 5,654,000 A | * | 8/1997 | Poli et al. .................... | 424/450 |
| 6,143,321 A | * | 11/2000 | Needham et al. ........... | 424/450 |
| 6,525,102 B1 | * | 2/2003 | Chen et al. ................. | 424/85.2 |

OTHER PUBLICATIONS

Bassett et al, The Journal of Urology, vol. 135, pp. 612-615, 1986.*

Hayashi, et al., *Temperature-Dependent Associating Property of Liposomes Modified with a Thermosensitive Polymer*, Bioconjugate Chem., 1998, vol. 9, No. 3, pp. 382-389.

Johnsson, et al., *Effect of PEO-PPO-PEO Triblock Copolymers on Structure and Stability of Phosphatidylcholine Liposomes*, Langmuir, 1999, vol. 15, No. 19, pp. 6314-6325.

Kostarelos, et al., *Physical Conjugation of (Tri-) Block Copolymers to Liposomes Toward the Construction of Sterically Stabilized Vesicle Systems*, Langmuir, 1999, vol. 15, No. 2, pp. 369-376.

Alexandridia et al.., *Micellization of Ploy (ethylene oxide)-Poly (propylene oxide)-Poly (ethylene oxide) Triblock Copolymers in Aqueous Solutions: Thermodynamics of Copolymer Association*, Macromolecules, 1994, vol. 27 No. 9, pp. 2414-2425.

* cited by examiner

Primary Examiner—Gollamudi S. Kishore
(74) Attorney, Agent, or Firm—Hodgson Russ LLP; Ranjana Kadle

(57) ABSTRACT

The present invention provides a liposomal composition for targeted delivery of drugs. The composition comprises large unilamellar vesicles (LUV) encapsulating poloxamers and one or more delivery agents. The composition and concentration of the poloxamer inside the LUVs is such that upon heating to temperatures above the critical micellar temperature of the poloxamer, the LUVs becomes leaky causing release of the encapsulated drug. The present invention also provides a method for delivery of agents to targeted sites and a method for preparing the LUVs suitable for use according to the method described herein.

26 Claims, 9 Drawing Sheets

TEMPERATURE CONTROLLED CONTENT RELEASE FROM LIPOSOMES

This invention was made with Government support under grant no. GM 30969 awarded by the National Institutes of Health. The Government has certain rights in the invention.

FIELD OF THE INVENTION

This invention relates generally to the field of drug delivery and more particularly provides a liposomal composition and method for temperature controlled release of contents.

DESCRIPTION OF RELATED ART

Throughout the application, references are cited as numerals with the full citations being provided at the end of Detailed Description of Invention.

Liposomes have been extensively used in the past decade as drug-carriers [1]. Desired properties of efficient carriers include the ability to evade the mononuclear phagocyte system (MPS) to prolong the circulation half-life ($t_{1/2}$), and preferential release of the encapsulated drug at the targeted site. Use of sterically stabilized liposomes has increased the liposome circulation time considerably [2,3]. Fusogenic liposomes have been developed [4,5] for cytoplasmic delivery of membrane-impermeable molecules. Controlled release of internal content from a suitably designed stimulus-sensitive liposome can be achieved by using various stimuli, such as temperature [6–9], pH [10–12] and light [13,14].

Different approaches have been used to produce temperature-sensitive liposomes for controlled release, such as use of the phase transition property of the constituent lipids [9], most notably dipalmitoyl-phosphatidylcholine (DPPC) which has a phase transition temperature of 42.5° C. In order to reduce the drug leakage from these liposomes, cholesterol is commonly added as a lipid component. The addition of cholesterol reduces the thermal sensitivity of DPPC in cholesterol-containing liposomes. This technique has met with various degrees of success [9, 27]

Another effective method of controlling the release from liposomes is the use of polymers [7,8,15]. In one study, poloxamer molecules were added to the outside of the liposomes and their adsorption to the liposomes was studied One of the polymers used has been poloxamer, which can cause moderate to severe release around the physiological temperature [16,17]. However, no temperature-dependent study was conducted.

Temperature controlled content release from phosphatidylcholine (PC) liposomes coated with a copolymer of N-isopropylacrylamide (NIPAM) has been attempted by Kim et al. [7]. Results from that study show that the extent of release is quite low (up to ~35%) without the aid of gel-to-liquid crystalline phase transition. Another study [8] shows the use of poly(NIPAM) coated di-oleoylphosphatidylethanolamine (DOPE) liposomes to achieve temperature triggered content release. This study relies on the stability imparted by the copolymer associated with DOPE at temperatures below the lower critical solution temperature (LCST) of the copolymer. Being a non-bilayer-forming lipid, DOPE does not form stable liposomes without the copolymer at the temperatures studied. The system becomes unstable at temperatures above the LCST due to a reduction in the stabilizing effect of the copolymer.

U.S. Pat. No. 5,720,976 to Kim discloses liposomes coated with poloxamers. While the poloxamer will make the liposomes leaky, the requirement of poloxamer on the outside of the liposomes makes its application in vivo difficult.

U.S. Pat. No. 6,200,598 to Needham discloses liposomes prepared using dipalmitoylphosphatidylcholine (DPPC) as the primary phospholipid and monopalmitoylphosphatidylcholine (MPPC) as the lysolipid where the ratio of DPPC:MPPC is about 99:1 to 60:40. Release of entrapped agent occurs at temperatures above gel-liquid crystalline phase temperature of the phospholipid mixture. The temperature at which the release of entrapped agents occurs is close to the phase transition temperature of DPPC of 41.5° C. The release of entrapped agents is only possible in a very limited range of temperatures.

Despite the above advances, efficient temperature controlled content release from liposomes has not been achieved for in vivo application and there continues to be a need for effective drug delivery methods using liposomes.

SUMMARY OF THE INVENTION

The present invention provides a liposomal composition for targeted delivery of drugs. The composition comprises large unilamellar vesicles (LUV) encapsulating poloxamers and one or more agents for delivery. Poloxamers do not significantly associate with the liposome bilayer at temperatures below their critical micellar temperature (CMT). However, above CMT, poloxamers partition into the LUV bilayer, causing defects in the bilayer leading to its eventual disruption. Therefore, in one embodiment, the poloxamer has a CMT around the physiological temperature. The concentration of the poloxamer inside the LUVs is such that upon incorporation of the poloxamer into the LUVs, the LUVs becomes leaky causing release of the encapsulated drug. In one embodiment, the poloxamer Pluronic F127 (M.W. ~12,600, $PEO_{98}$—$PPO_{67}$—$PEO_{98}$) was used because of its high molecular weight and desired hydrophilic-hydrophobic balance (HLB), both factors reducing the detergent-like toxicity, and a CMT around the physiological temperature.

The present invention also provides a method for delivery of agents to targeted sites. The method comprises (1) preparing large unilamellar vesicles encapsulating the agent and poloxamer molecules, wherein the concentration of the poloxamer is such that upon incorporation of the poloxamer molecules into the LUV membrane at a temperature above the CMT, the membrane becomes leaky causing the release of the encapsulated Delivery Agent; (2) administration of the LUVs to the individual; and (3) increasing the temperature of the target site to effect release of agent from the LUVs. As an example, the release of tracer molecules of different molecular weights, from liposomes of different lipid compositions is described.

The present invention further provides a method for preparing the LUVs suitable for use according to the method described herein. The method of preparation comprises the steps of forming multilamellar vesicles (MLV)s in the presence of one or more agents and poloxamer molecules, preparing LUVs therefrom such that the poloxamer and the drug are encapsulated within the LUVs. Unencapsulated i.e., free agent and poloxamer molecules are then separated from the LUVs. The poloxamer is selected so that it has a CMT around the physiological temperature. The concentration of the poloxamer inside the LUV is such that upon incorporation into the LUV membrane, the LUV becomes leaky.

DETAILED DESCRIPTION OF THE INVENTION

Figure 1:
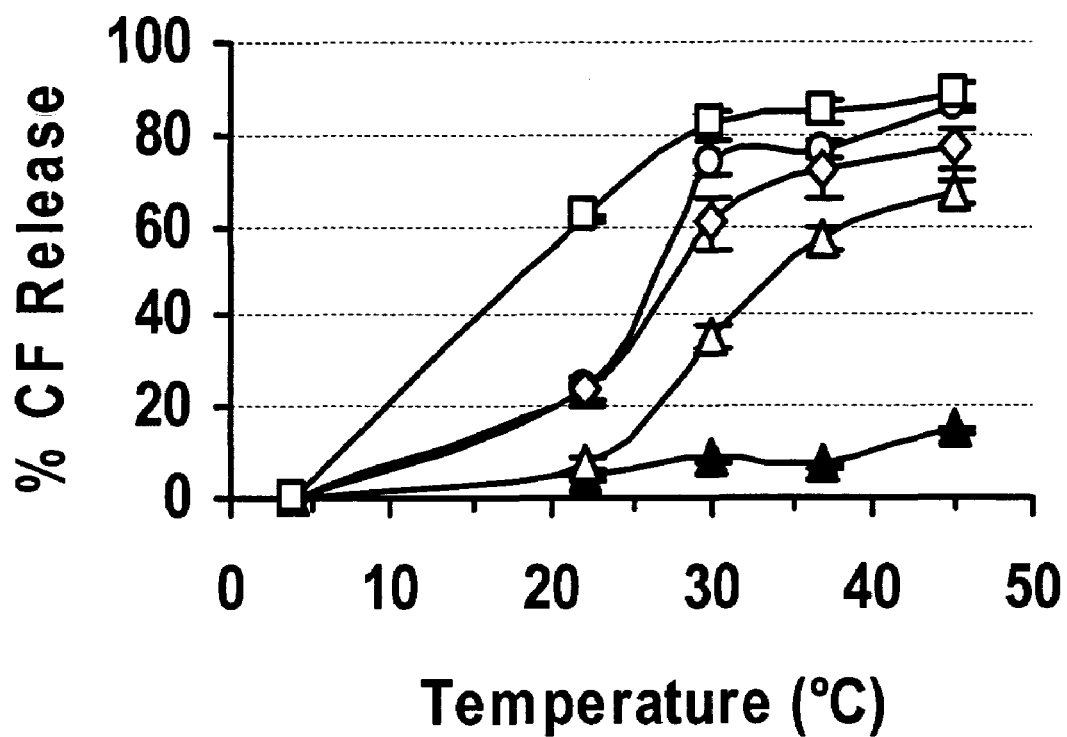
FIG. 1 is a representation of the percent carboxyfluorescein (CF) release from DOPC LUVs at different temperatures. All LUVs were made of DOPC and 5 mole percent cholesterol. The encapsulated solution comprises of CF and different percent (w/v) Pluronic F127. The "control" sample (solid triangle) has no Pluronic (0%). The "F127" samples are: 0.02% (open triangle), 0.04% (open diamond), 0.08% (open circle) and 0.16% (open square). Error bar represents variations among at least three repeating samples.

Definitions:

The term "liposomes" or "vesicles" or "liposome vesicles" as used herein means structures having lipid containing membranes enclosing an aqueous interior. Structures having more than one layer of membranes are termed multilamellar vesicles (MLVs). Structures having one layer of membrane are termed unilamellar vesicles. The unilamellar vesicles may be large unilamellar vesicles (LUVs) or small unilamellar vesicles (SUVs).

The term "large unilamellar vesicles" or "LUVs" as used herein means unilamellar vesicles having a diameter of between about 100 nm to 1.0 μm.

The term "critical micellar temperature" or "CMT" as used herein means the temperature above which the poloxamer molecules by themselves exist in aqueous medium as micells, and below which the poloxamer molecules by themselves exist as individual molecules (unimers) in solution.

The term "poloxamer" as used herein means block co-polymers of polyethylene oxide (PEO)-polypropylene oxide (PPO)— polyethylene oxide (PEO), each block can be of different molecular weights.

The term "Delivery Agent" as used herein means any chemical compound that is encapsulated in the LUVs for delivery to a target site. Examples of Delivery Agents are provided below.

The term "Stealthing" as used herein means a process of coating the surface of liposomes with a layer of polymer molecules that enables the liposomes to avoid being removed from the circulation system of the body by the mononuclear phagocytic system of the body, thus prolonging their circulation time as compared to that of non-coated liposomes.

The present invention provides a composition for temperature sensitive liposome vesicles. The composition comprises large unilamellar vesicles (LUVs) encapsulating a composition comprising one or more Delivery Agents and a plurality of poloxamer molecules wherein the poloxamer is at a concentration such that upon increasing the temperature to above the CMT, the poloxamer molecules are incorporated into the LUV membrane thereby making the LUV leaky which in turn effects release of the encapsulated agent.

The lipids used include but not limited to phospholipids such as phosphatidylcholine, phosphatidylserine, phosphatidylglycerol, phosphatidylethanolamine, phosphatidylinositol and their mixtures, and with added sphingolipids, glycolipids, fatty acids and cholesterol at various proportions if desired.

Poloxamers are polyethylene oxide (PEO)-polypropylene oxide (PPO)-polyethylene oxide tri-block co-polymers of different molecular weights. The hydrophobic PPO group in the middle links the two hydrophilic PEO groups. The amphiphilic nature of the poloxamer renders itself extremely useful in various applications as emulsifiers and stabilizers [18]. Poloxamers do not associate with the bilayer at temperatures below the CMT. However, above the CMT, they partition into the bilayer. Poloxamers of different molecular weights and with different hydrophilic-lipophilic balance (HLB) have different CMTs [19]. This monomer-to-micellar transition process is extremely temperature-sensitive. With a slight change of temperature, the corresponding critical micellar concentration (CMC) may change by several orders of magnitude [20].

An example of a poloxamer useful for this invention is Pluronic F127 (M.W. ~12,600, $PEO_{98}$—$PPO_{67}$—$PEO_{98}$). This poloxamer is useful because of its high molecular weight, desired HLB (>24) and a CMT around the physiological temperature between 33° C. and 43° C., at a concentration of 0.01 to 0.1% w/v. Other poloxamers satisfying these criteria include, but are, and not limited to, F87, F88, F 98, F108, and P188.

In the present invention, the concentration of the poloxamer inside the LUVs is such that upon elevation of the temperature to within about 5 degrees above the CMT, the poloxamer is able to incorporate into the lipid bilayer of the LV so as to make it leaky. Suitable concentration range of the poloxamer is between 0.01 to 0.2% w/v, and may differ somewhat from poloxamers to poloxamers.

The LUVs of the present invention can be prepared by standard techniques. The commonly used extrusion technique is as follows. Lipid components (such as phopatidylcholine and cholesterol) in chloroform are mixed and dried to form a lipid film. The film is rehydrated in the presence of the drug and poloxamer. The MLVs so formed are extruded to form LUVs of desired size. Generally, LUVs in the range of 100 to 400 nm are useful for the present invention. By using this technique, the concentration of the poloxamer inside the LUV can be controlled. By varying the concentration, the desired CMT for a particular poloxamer can be obtained. It should be noted that while the LUVs of the present invention can be prepared by other techniques such as detergent dialysis, fusion of SUVs, reverse evaporation and ethanol injection, it is preferable to encapsulate the poloxamer molecules along with the agent as described herein instead of co-solubilization with lipids since it is difficult to control the concentration of the poloxamer within the LUV.

An advantage of the present invention over prior temperature-sensitive liposome technologies is the ability to control the temperature at which release of entrapped agents occurs. This is achieved by a simple adjustment of the concentration of the specific poloxamer used. The entrapped content-release temperature can be adjusted to suit specific cases. Thus, this invention can be used to control liposomal content release under conditions of hypothermia or hyperthermia (such as where an individual has fever).

The LUVs are separated from the free agent and poloxamer by standard techniques such as filtration or dialysis. The filtration method entails passing the sample through a filter device (such as Millipore® filters), with the filter pore size smaller than the LUV, such that vesicles are retained behind the filter while free agents and poloxamers are filtered through. The dialysis method entails enclosing the sample within a dialysis bag or device, with the membrane pore size smaller than the LUV, such that free agents and poloxamers may diffuse through to the dialysis medium, and vesicles are retained. In addition, veisicles may be separated from free agents and poloxamers by size exclusion column chromatography. MLV can be separated by differential centrifugation.

The agents that can be delivered by the liposomal composition of the present invention include therapeutic drugs, pharmacologic active agents, nutritional molecules, diagnostic agents, image contrast agents and any other molecules that is desired to be delivered to a particular physiological site. Therapeutic agents include antibiotics, anti-tumor agents, anti-inflammatory agents, anti-neoplastic agents, anti-microbial agents, anti-viral agents, immunosuppressive agents, antisense oligonucleotides, plasmids, enzymes, hormones, nanoparticles and the like.

Liposomes of the present invention can be administered using methods that are well known in the art. Such methods include delivery of the liposomal composition to the bloodstream by intravenous administration or direct delivery to the target site. For example, the liposomal composition may be delivered directly to a tumor site or a site of inflammation.

Once liposomes have been delivered to the site either via normal blood flow or by direct administration at the site, heat can be applied to the site. Heating may be achieved by heat pad or heat lamp from the skin surface, or by focused microwave or laser or ultrasound applications.

The present invention will be better understand from the following embodiments which are intended to be illustrative and not restrictive in any way.

EXAMPLE 1

This embodiment describes the preparation of LUVs useful for the present invention. To illustrate this embodiment, the preparation of LUVs using the poloxamer Pluronic F127 (BASF (Mount Olive, N.J.)) is described. The lipids di-oleoyl phospatidylcholine (DOPC), cholesterol and DS(PEG5000)PE were purchased from Avanti Polar Lipids Inc. (Alabaster, Ala.).

All liposomes were made with DOPC/cholesterol and different mole percent of Pluronic F127. Multi lamellar vesicles (MLV) and large unilamellar vesicles (LUV) were made for different experiments. A Delivery Agent and Pluronic F127 were mixed with buffered marker solution (60 mM NaCl, 5 mM phosphate buffer, pH 7.4), where needed, and entrapped inside the vesicles as follows. Lipids (phophatidylcholine and cholesterol (with about 1 mol % of DS(PEG5000)PE or other PEGylated lipids to made it stealth), in chloroform, were mixed in a round-bottomed flask and dried under a gentle stream of nitrogen gas to form a thin layer on the flask wall. The film was dried further in a vacuum chamber, for 3 to 4 hours, to remove any remaining solvent. MLVs were formed by first re-suspending the dry lipid film with buffered dye solution, with or without Pluronic F127, with or without a drug, followed by vortexing. LUVs were formed by extruding the MLV solution through a 0.2 µm poly-carbonate filter (Millipore, Bedford, Mass.), for fifteen times or more. The LUVs prepared by this method are between about 100 to 400 nm. All the liposomes were prepared and kept inside a cold room (4° C.) until being used in the experiment. Within experimental error, the amounts of CF or BSA-FITC encapsulated are not dependent on the F127 concentration, as measured by the fluorescence after complete lysis of liposomes by Triton X-100 after the experiment.

EXAMPLE 2

This embodiment describes the measurement of release of a Delivery Agent from the liposomal composition of the present invention. To illustrate this embodiment, the release of CF from the LUVs was determined. CF release is a widely used method to determine liposome permeability [21]. Fluorescence of CF, at 100 mM concentration, is self-quenching, and release of the marker in the environment increases the fluorescence due to dilution de-quenching. A solution of 100 mM CF (with 60 mM NaCl and 5 mM phosphate buffer), with appropriate percent (w/v) of Pluronic F127, was added to the dry DOPC with different mole percent of cholesterol to form the MLVs. The liposomes were then extruded to form LUVs, as described in Example 1. Unencapsulated CF and the LUVs were separated using a Sephadex G-50 column. An elution buffer comprising of 217 mM sucrose and 5 mM phosphate was used in the column to balance the internal osmotic pressure of the liposomes. All the preparation steps were performed inside a cold room (4° C.).

For each experimental sample, 250 μl of the liposome fraction was further diluted, using the same elution buffer as above, to a final solution volume of 3 ml. Fluorescence intensity of the CF was measured using a SLM 8000 fluorimeter. The initial fluorescence (Ex. 492 nm, Em. 518 nm) intensity of a sample at 4° C. was recorded. The sample temperature during measurement in the fluorimeter was maintained at the desired level using an adjustable thermostat-controlled heating/cooling unit. All other samples used in the same experiment were kept at their respective desired temperatures in water baths. Before measurement, each sample was kept for 15 min in the fluorimeter chamber to bring it to a thermal equilibrium. At and beyond this time, the fluorescence readings had reached steady values, indicating an equilibrium release was achieved. Fluorescence of the CF is also temperature dependent. Thus, the fluorescence intensities obtained in the experiments were corrected for any temperature effect. Increase in fluorescence intensity are preferably converted to percent release of CF if all the measured concentration values fall on the linear part of the fluorescence de-quenching curve. After the release measurement, 15 μl solution of 10% Triton X-100 was added to the liposome solution in order to completely lyse the liposomes. Fluorescence intensity was measured again after lysis. The percent CF release value of a sample at a temperature t was calculated using the equation:

$$\%CF \text{ release} = (I_S - I_0)/(I_T - I_0) * 100\% \quad (1)$$

where $I_S$=fluorescence intensity value of the sample at temperature t, $I_0$=fluorescence intensity value of the sample at 4° C., and $I_T$=total fluorescence intensity value of the sample at temperature t measured after complete lysis of the liposomes using Triton X-100.

The data for this experiment on the effect of different weight percent of encapsulated Pluronic F127 on the release of CF, at different temperatures is shown in FIG. 1. The control (0% Pluronic) sample shows minimal release throughout the experimental temperature range. All the other four curves represent samples containing encapsulated Pluronic: 0.02, 0.04, 0.08 and 0.16% (w/v; 0.625, 1.25, 2.5 and 5 mole % of lipid in the initial mixture). The sample containing 0.02% (w/v) Pluronic starts showing significant release of about 35% at 30° C., and increases gradually to 64% at 45° C. The sample containing 0.04% (w/v) Pluronic shows considerable release of about 23% at 22° C. The release increases to 60% at 30° C. and further to 77% at 45° C. The sample containing 0.08% (w/v) Pluronic has release of 23% at 22° C. The % release jumps to 76% at 30° C. and then levels off. The 0.16% (w/v) Pluronic sample shows severe release (60%) at 22° C. The percent release increases to a maximum of 87% subsequently. There is a general trend in the content release of these samples. CF release is higher with increasing percent of Pluronic content. In addition, significant release starts at lower temperatures with increasing percent of Pluronic content.

Figure 2:
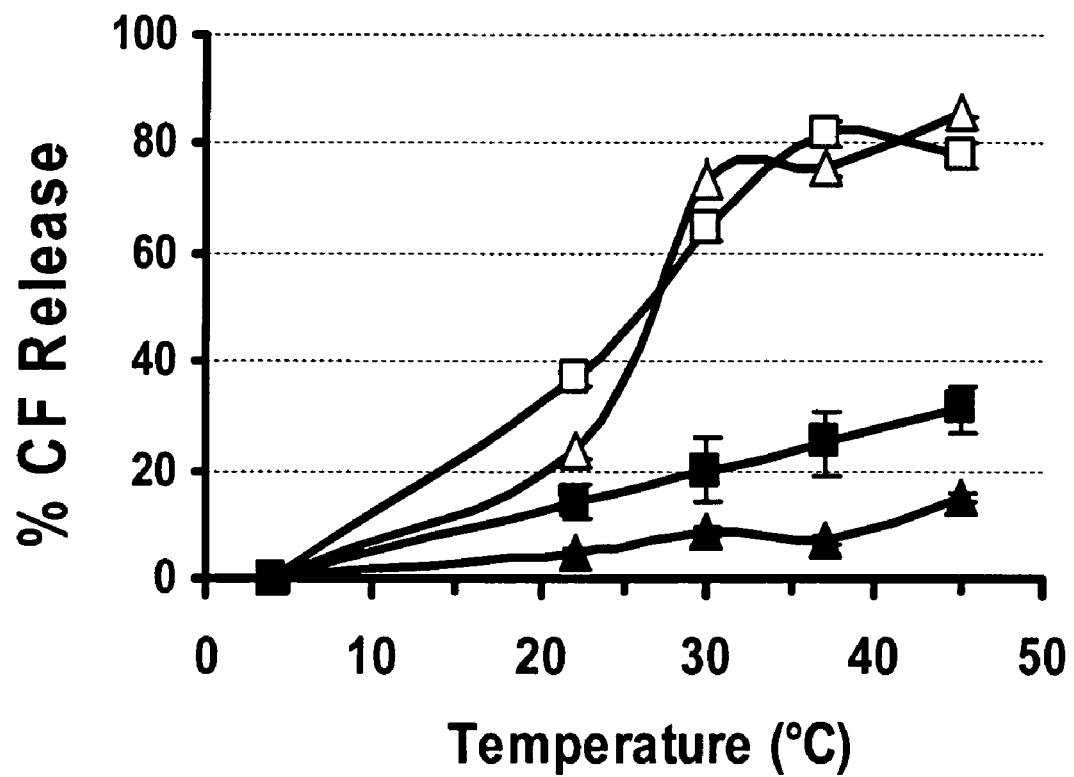
FIG. 2 is a representation of the percent CF release from polyethylene glycol (PEG) containing DOPC LUVs at different temperatures. All LUVs are made of DOPC and 5 mole percent cholesterol. The PEG samples have additional 1 mole percent of the PEGylated lipid PEG(MW5000)-conjugated-DSPE (DS(PEG5000)PE) in the lipid composition. The encapsulated solution comprises of CF alone (control) or CF with 0.08% (w/v) Pluronic F127 (F127). The "control" samples are: no PEG (solid triangle) and with PEG (solid square). The "F127" samples are: no PEG (open triangle) and with PEG (open square). Error bar represents variations among at least three repeating samples.

The effect of DS(PEG5000)PE on the release of CF was also determined. Stealth liposomes are effective in increasing the liposome circulation time [2,3] giving the liposomes increased opportunity to deliver internal content at the target site. Therefore, it is important to test content release in a stealth liposome system, simulating in vivo application. This experiment compares the internal content release of DOPC (with 5 mole percent cholesterol) LUVs in the presence and absence of PEG-conjugated lipids. 1 mole percent DS(PEG5000)PE, enough to make a bilayer stealth [23], was added to DOPC and cholesterol to form PEG containing LUVs. The results are shown in FIG. 2. Samples were made either without PEG lipid (triangular symbols), or with 1 mole percent DS(PEG5000)PE (square symbols). The two "control" curves (with filled symbols) represent liposomes containing no Pluronic F127, while the two "F127" curves (with open symbols) represent liposomes with 0.08% (w/v) of encapsulated Pluronic. Although both the "control" samples show increase in release with temperature, the percent release is much lower in comparison to the "F127" samples. The "control" sample, with PEG lipids, shows 30% release at 45° C. Both the "F127" samples show release characteristics similar to each other. The "F127" sample without PEG lipid shows about 20% release at 22° C. This is followed by a significant increase in release (76%) at 30° C., leveling off subsequently. The "F127" sample with PEG lipid has a 38% release at 22° C. The release gradually increases with increasing temperature, reaching a maximum of about 80%.

Figure 3:
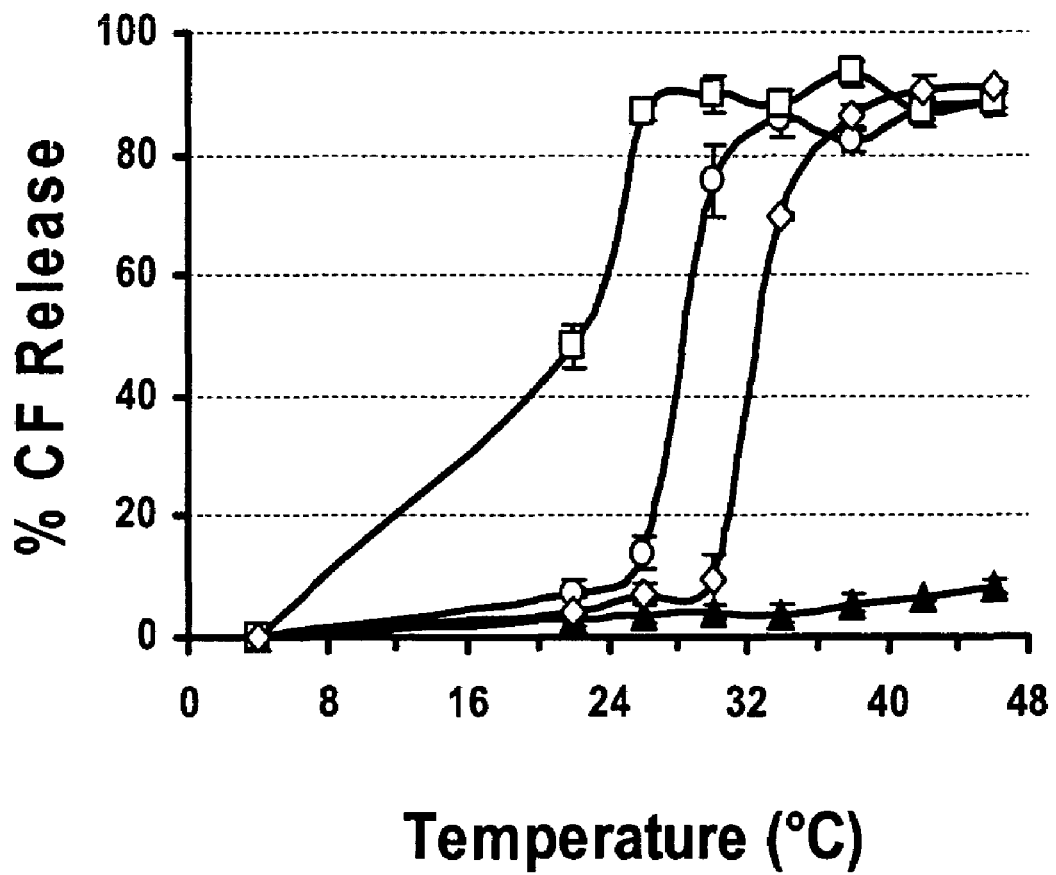
FIG. 3 is a representation of the percent CF release from high cholesterol containing—DOPC LUVs at different temperatures. All LUVs are made of DOPC: cholesterol (50:50 by mole percent). The encapsulated solution comprises of CF and different percent (w/v) Pluronic F127. The "control" sample (solid triangle) has no Pluronic (0%). The "F127" samples with different % (w/v) of Pluronic are: 0.04% (open diamond), 0.08% (open circle) and 0.16% (open square). Error bar represents variations among at least three repeating samples.
Figure 4:
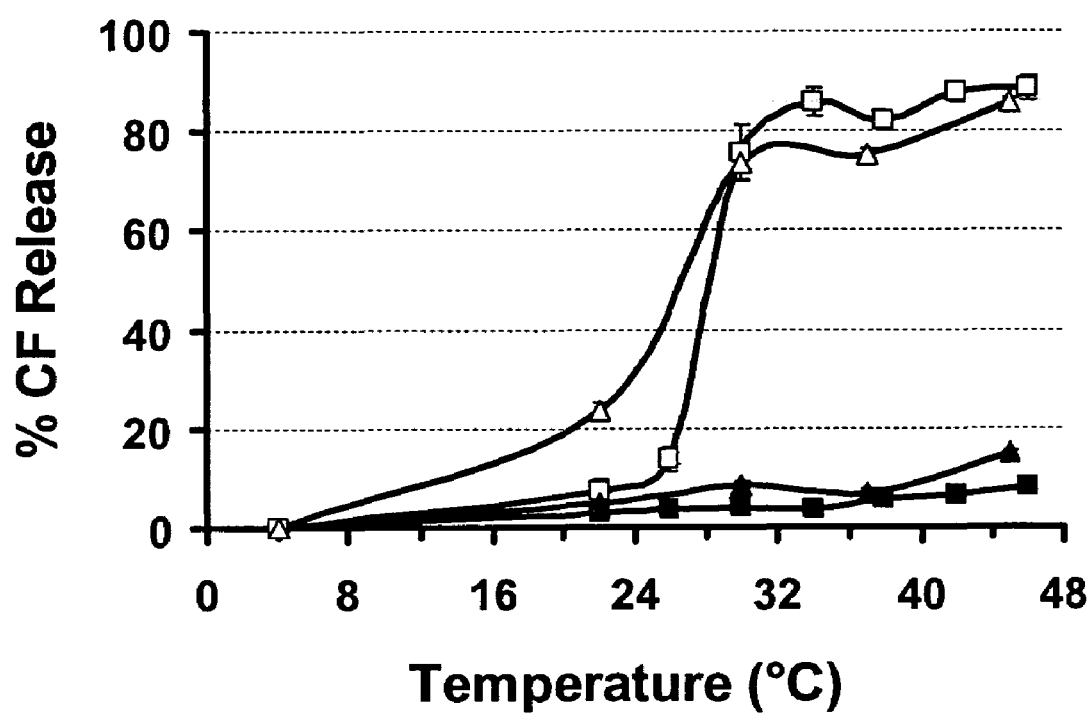
FIG. 4 shows a comparison of temperature-dependent CF release from DOPC LUVs, with different percent of cholesterol in the lipid composition. The LUVs are made of DOPC: cholesterol (95:5 or 50:50 by mole percent). The encapsulated solution comprises of CF with 0% or 0.08% (w/v) Pluronic F127. The "control" samples, without Pluronic, contain: 5% cholesterol (solid triangle) and 50% cholesterol (solid square). The "F127" samples, with 0.08% (w/v) of Pluronic contain: 5% cholesterol (open triangle) and 50% cholesterol (open square). Error bar represents variations among at least three repeating samples.

The release of CF from DOPC LUVs containing 50 mole percent of cholesterol was also investigated. High mole percent of cholesterol (up to 50%) is frequently used in making liposomes for drug delivery [24,25]. Cholesterol helps in attaining increased stability of the liposome as well as reduced leakage of the encapsulated drug [27]. Thus, this experiment was designed to determine whether increase in amount of cholesterol in the lipid composition affects the CF release from LUVs. All samples consisted of LUVs made from a lipid composition of DOPC: cholesterol (50:50 by mole). The encapsulated CF solution contained different percent (w/v) of Pluronic F127 for four different samples: (0, 0.04, 0.08 and 0.16% w/v). The results are plotted in FIG. 3. The "control" sample, without Pluronic, shows very little release. The CF release in this sample is only about 8% at 46° C. At a concentration of 0.04% (w/v) of encapsulated Pluronic, the release is minimal, up to 30° C., after which the content release increases abruptly to 70% at 34° C. At 38° C., the internal content release reaches a plateau of 86%. For the sample containing 0.08% (w/v) of encapsulated Pluronic, the release is small until 26° C. The release reaches a value of 84% at 34° C. and then levels off. The sample with 0.16% (w/v) Pluronic has a 46% CF release at 22° C. It reaches a value of about 90% at temperatures of 26° C. and above. FIG. 4 shows a comparison between the CF release experiments with 5 mole percent and 50 mole percent cholesterol. The "control" samples, without F127, are very similar to each other. Each of the F127 samples contain 0.08% (w/v) of Pluronic F127. The "F127" sample with 50 mole percent cholesterol shows a sharper transition than that of the 5 mole percent one.

EXAMPLE 3

The experiments described in Example 2 demonstrate release of the marker CF, which has a molecular weight of 376. This embodiment demonstrates that considerably larger molecules can also be released from the LUVs of the present invention by increasing the temperature. To illustrate this embodiment, the release of BSA-FITC, which has a molecular weight of about 66,000, from LUVs was measured by donor fluorescence quenching due to fluorescence resonance energy transfer (FRET) [22]. The fluorescence de-quenching of BSA-FITC was not used because high concentration of BSA-FITC leads, to some extent, to aggregation of the encapsulating MLVs. Lipid solutions comprising DOPC and cholesterol (50:50 by mole) were used to form the MLVs. Fifty mole percent cholesterol was used, since that composition gave the best encapsulation of BSA-FITC among all different compositions. A solution of 5.5 µg/ml of donor BSA-FITC (with 100 mM NaCl and 5 mM phosphate buffer) at a non-quenching concentration, with appropriate percent (w/v) of Pluronic F127, was added to the dry lipids to form the MLVs. The liposomes were then extruded to form LUVs, as described in Example 1. In order to remove any unencapsulated BSA-FITC molecule, the LUVs were separated by a Sephadex G-100 column, and appropriate fraction was collected and used for the assay. An elution buffer comprising of 125 mM NaCl and 5 mM phosphate was used in the column to balance the internal osmotic pressure of the liposomes. All the preparation steps were performed inside a cold room (4° C.).

For each sample, 50 µl of the liposome fraction was further diluted, using the same elution buffer as above, to a final solution volume of 3 ml. Fluorescence intensity spectrum of the BSA-FITC was measured and recorded using a SLM 8000 fluorimeter. The excitation wavelength was kept at 492 nm, excitation maximum of the donor fluorophore FITC, throughout the experiment. All the fluorescence emission intensity readings were taken at the emission maximum of the donor BSA-FITC (519 µm). The spectra of samples at 4° C. were first recorded. After recording the initial fluorescence emission intensity of a sample of BSA-FITC alone, 100 µl of the acceptor Dextran-TR solution (1 mg/ml) was added to the sample. The fluorescence emission intensity of the sample containing both the donor and the acceptor was then recorded. A 10 µl solution of 10% Triton X-100 was added to the sample solution in order to completely lyse the liposomes. Fluorescence intensity was recorded again after lysis. The procedure was repeated for samples treated at other temperatures.

The efficiency (E) of donor quenching due to FRET was calculated according to [22]:

$$E = [1-(F_{da}/F_d)]*100 \quad (2)$$

where, $F_{da}$ is fluorescence intensity of the donor in presence of the acceptor; and $F_d$ is fluorescence intensity of the donor in absence of the acceptor.

Efficiency of donor quenching can be converted to percent release when there is enough acceptor molecules present in the medium to allow energy transfer from each donor molecule released in the medium. Since the concentration of TR in the sample solution was more than 350 times the maximum concentration of FITC, the above assumption for such conversion would be valid. Thus, we can calculate the % BSA-FITC release of a sample at a temperature t, using the equation:

$$\% \text{ BSA-FITC release} = (E_S-E_{ini})/(E_{Triton}-E_{ini})*100\% \quad (3)$$

where $E_S$=efficiency of donor quenching of the sample at temperature t;

$E_{Triton}$=efficiency of donor quenching of the sample at temperature t after complete lysis of the liposomes using Triton X-100; and $E_{ini}$=efficiency of donor quenching of the sample at 4° C.

The fluorescence intensity values were corrected for the background and inner filter effect. The sample temperature was maintained during measurement at the desired level by a thermostat controlled cuvette holder inside the fluorimeter. All other samples, waiting to be measured, were kept at their respective desired temperature in water baths. Before measurement, each sample was kept for 15 min in the fluorimeter chamber to bring it to a thermal equilibrium.

Figure 5:
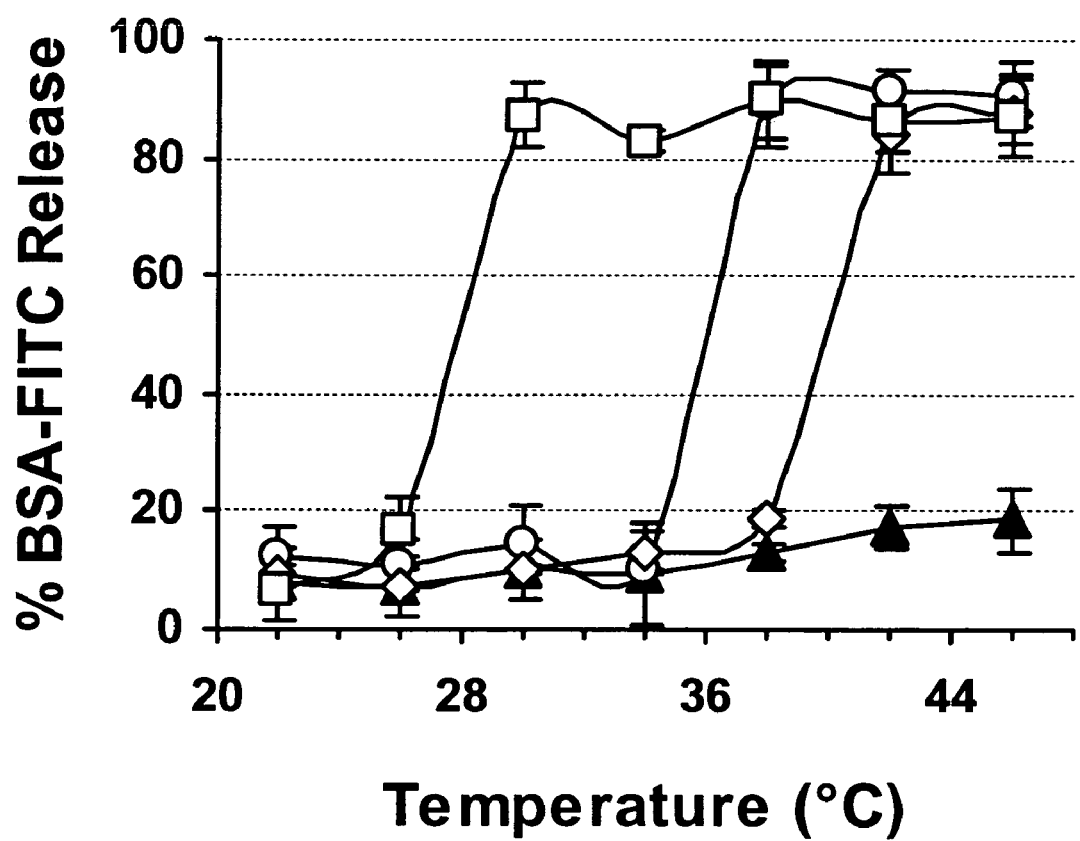
FIG. 5 is a representation of the percent bovine serum albumin-fluorescein isothiocyanate (BSA-FITC) release from DOPC LUVs at different temperatures. All LUVs are made of DOPC:cholesterol (50:50 by mole percent). The encapsulated solution comprises of BSA-FITC and different percent (w/v) Pluronic F127. The "control" sample (solid triangle) has no Pluronic (0%). The "F127" samples contain different % (w/v) of Pluronic: 0.04% (open diamond), 0.08% (open circle) and 0.16% (open square). Error bar represents variations among at least three repeating samples.

The results of the experiment are shown in FIG. 5. All samples consisted of LUVs, made from a lipid composition of DOPC and cholesterol (50:50 by mole), encapsulating the BSA-FITC solution with different % (w/v) of Pluronic. The "control" curve represents sample with no encapsulated Pluronic. The other three curves correspond to samples with 0.04, 0.08 and 0.16% (w/v) of encapsulated Pluronic, respectively. At 22° C., all four samples show small percent release, ranging from 6 to 12%. The "control" sample has a small percent release in the experimental temperature range, maximum being 19% at 46° C. The sample containing 0.04% (w/v) of Pluronic shows low percent release up to 38° C. temperature. After that the content release jumps to 84% at 42° C. and levels off. Sample with 0.08% (w/v) of Pluronic shows similar release characteristics except that the sudden increase in % release is at 34° C., instead of 38° C. as observed in the case of the 0.02% (w/v) sample. At 22° C., the 0.16% (w/v) Pluronic sample leaks 6% and then increases to about 17% at 26° C. Eventually the release increases to about 86% at 30° C., subsequently leveling off. These results indicate the disruption of the LUV membrane is such that even large molecular weight agents can be delivered to the target site. Accordingly, the present invention can be used for delivery of small as well as large agents.

Figure 6:
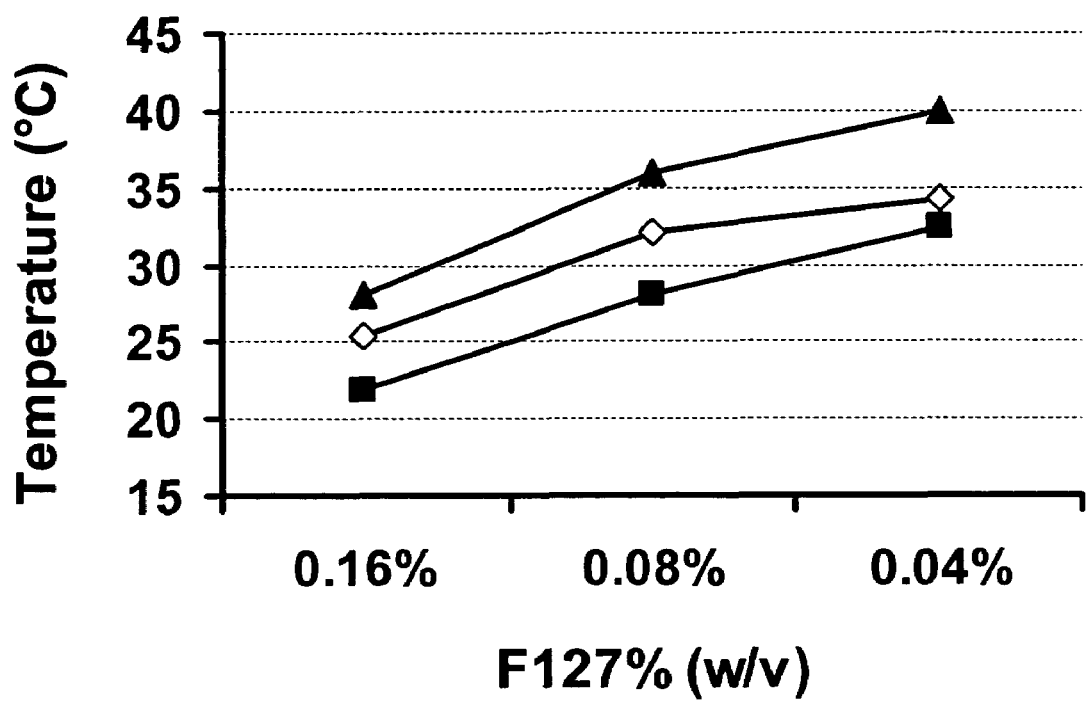
FIG. 6 shows a comparison of inflection points of content release data for CF and BSA-FITC, for samples made of DOPC:cholesterol (50:50 by mole percent), at different percent (w/v) of Pluronic F127 concentration. The corresponding CMTs are obtained from previously published result [20]. The curves represent: onset for CF release (solid square), CMT value [20] (open diamond) and onset for BSA-FITC release (solid triangle).
Figure 7:
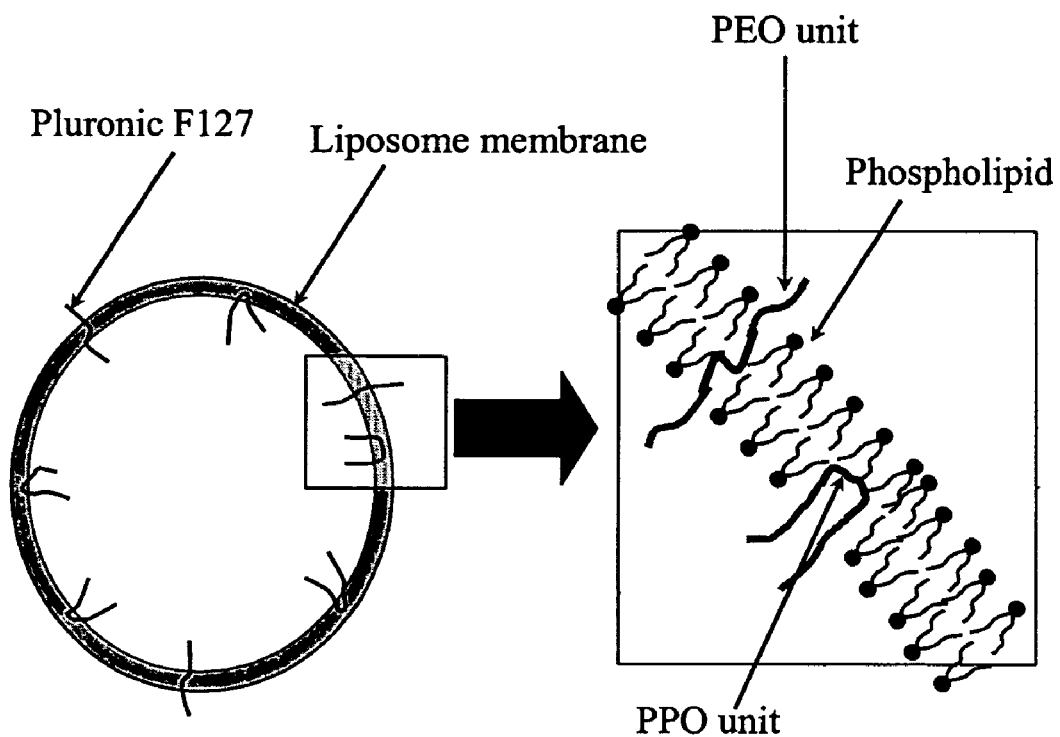
FIG. 7 is an illustration of the poloxamer molecules in the liposomal bilayer.

While not intending to be bound by any particular theory, the present data suggests that the onset temperature is governed by the concentration of encapsulated poloxamer. Thus, the onset of content release is triggered by the association of the poloxamer molecules with lipid bilayers at temperatures above the CMT. In further support of this hypothesis, the experimentally obtained onset temperature points were compared with experimentally obtained CMT values for free Pluronic F127 at corresponding concentrations [20]. The results obtained from experiments with liposomes made of DOPC (with 50% cholesterol) were used, since both CF and FITC-BSA data using this composition was available. The onset values for the present experimental results were calculated using the inflection point (i.e. mid-point) analysis of the curves with different percent (w/v) of Pluronic. FIG. 6 shows such a comparison. For any Pluronic F127 concentration, CF and BSA-FITC onset temperatures are, respectively, lower and higher than the known CMT values[20]. It could be expected that the onset temperature for the CF system to be lower than that of the BSA-FITC system, since CF would be released through smaller bilayer defects than BSA-FITC. For BSA-FITC, complete release is expected to take place at a higher temperature than CMT because such release needs significant bilayer disruption. Accordingly, the release temperatures for the particular concentration of the poloxamer can be obtained from empirical data.

EXAMPLE 4

This embodiment describes the release of a Cell-binding Agent from the liposomal composition of the present invention. The Cell-binding Agent is Lucifer Yellow (Molecular Probe, Eugene, Oreg.). Lucifer Yellow (LY) is a fluorescence marker dye and serves as an example of encapsulated, water soluble substance including drugs that binds to cell surfaces and could be internalized by cells. Liposomes were made by a slightly varied procedure as described in example 1. The lipid composition was 67% DOPC, 32% cholesterol, and 1% PEG 5000-POPE. 30 mg of lipids in chloroform solution was dried by a flow of nitrogen gas, then under a vacuum for 1 hr. A solution of LY, at a concentration of 3 ng/ml LY in 0.25 Osm Phosphate Buffered Saline (PBS) with 0.04% w/v of F127, was added to make MLV. The dried lipids were rehydrated by vortexing at 4° C. with 3 ml LY/F127 solution. LUVs were made by extrusion 10 times through a 400 nm pore size polycarbonate filter at 4° C. The free LY/F127 was separated from the encapsulated dye/poloxamer by G-25 column chromatography, with spin columns centrifuged at 1000×g for 2 minutes.

To measure temperature-dependent release of LY, 1 ml LY/F127 loaded LUV samples were aliquotted into plastic tubes and placed in hot water baths maintained at 21, 30, 33, 36, 39, 42, and 45° C. for 30 min respectively. After heating, samples were placed into centrifugal filter tubes and spun at 3,800 rpm for 1 hr at 4° C. to remove LUVs from released dye. Samples representing complete dye release were prepared by adding 30 µl of 2% triton X-100 solution and heated at 45° C. The amounts of LY released from samples treated at different temperatures were then assayed by fluorometer (Ex $\lambda$=427 nm, Em $\lambda$=500–600 nm).

Figure 8:
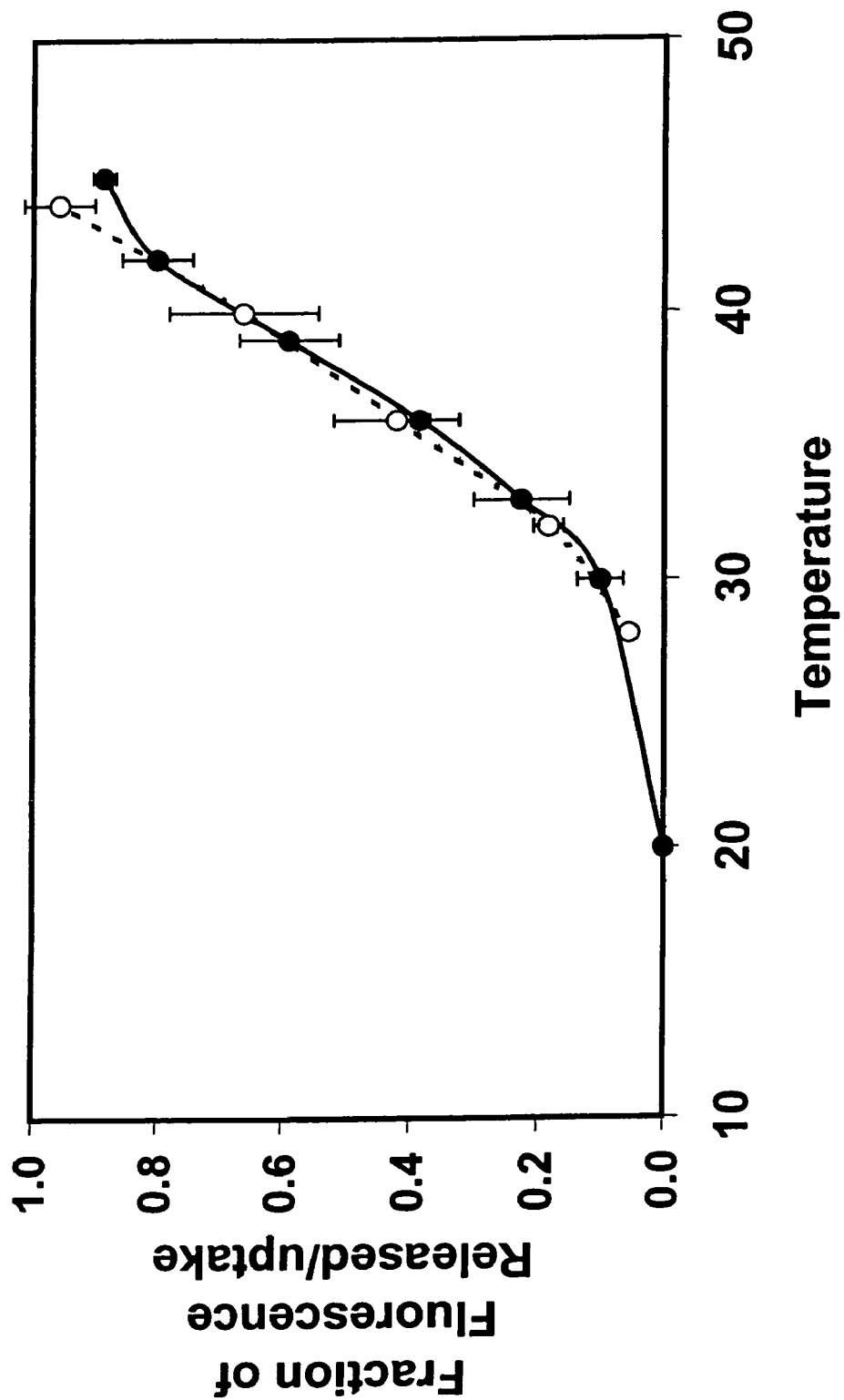
FIG. 8 is a representation of the release of LY from a poloxamer-containing LUV (●) and a representation of the preferential release of LY in a tumor (○) using the method of the present invention.

FIG. 8 (solid dots) shows the percentage of dye released from the samples heated to given temperatures. At 20° C., no detectable dye was released. Measurable release was observed at 30° C. and the release reached 80% at 42° C. and 88% at 45° C. The inflection point of LY release in this example is slightly different from those of CF and FITC-BSA in examples 2 and 3 because the differences in lipid composition, in the dye content and in the presence of salt in the solution [28].

The adhesion of released LY at given temperatures to cancer cells from the liposomal composition of the present invention was also studied. Colon cancer cells "Colon-26" were cultured in RPMI1640 with 7–10% fetal calf serum. Cells were treated with heated LY/F127 LUV samples as described below. Heating of LUV samples was performed as described in the last paragraph. After heating, the samples were allowed to cool down to 21° C. 1×10$^8$ cells were washed 3 times with PBS, scraped from petri dishes, vortexed to dissociate, and aliquotted into 21 plastic tubes per experiment with 500 µl of cells in PBS in each tube. 1 ml heat-treated LUV samples were added to each tube of cells to allow for binding of the LY to cell surfaces. The cells were shaken gently on a rotating platform for 4 hr. The tubes were centrifuged at 1000×g for 10 min. The supernatant was removed and the cells were washed three times with PBS to remove LUVs and unbound LY. 500 µl cell lysis buffer (4% triton X-100, 50 mM SDS, +10% ethanol in PBS) was added to each tube. Samples were vortexed and incubated at 40° C. for 24 hr. Samples were then assayed by fluorometer as described in the last paragraph.

FIG. 8 also shows the percentage of LY associated (surface-bound or internalized) with cells after treated with LY/F127 LUV that were heated to different temperatures (open circles). Only 5% of LY associated with the cells treated in 28° C. samples, whereas 95% was with the cells treated in 45° C. samples. The cell binding curve follows closely to the LY release curve, indicating most of the released LY ended up associating with cells.

EXAMPLE 5

This embodiment describes the association of a Cell-binding Agent to tumors in mice under heat treatment, using the liposomal composition of the present invention. The Cell-binding Agent is Lucifer Yellow (Molecular Probe, Eugene, Oreg.). Lucifer Yellow (LY) is a fluorescence marker and serves as an example of encapsulated, water soluble substance including drugs, that binds to cell surfaces and could be internalized by cells. Liposomes were made by the same procedure as described in example 4, except that LUVs prepared for in vivo experiments were extruded 3 times through an 800 nm filter, 3 times through a 400 nm filter, and 4 times through a 200 nm filter. For in vivo experiments, the eluted volume was then concentrated four-fold in a dialysis machine, using cellulose filters. Frozen Colon-26 cells were thawed and washed with PBS buffer. 1×10$^7$ cells were subcutaneously injected onto each hind leg of Balb/c mice. Tumors grew to about 1 cm after 3 weeks. The day preceding heat treatments, hair on the hind legs of the mice was removed with Nair® hair removal lotion. Immediately prior to treatment, mice were anaesthetized with 150 µl ketamine/xylazine solution. The tumor on one leg of the mouse was heated and the tumor on the other leg served as unheated control. Heating was accomplished by shining a heat lamp directly upon a piece of black felt affixed over the tumor. The area around the tumor was surrounded by 3 layers of aluminum foil. This ensured that radiative heating only occurred through the tumor surface. A needle probe thermocouple was inserted into the center of the tumor to be heated. Temperatures of unheated tumors were also taken. The heating was constantly monitored to maintain an intratumor temperature of 42.0±0.6° C. Once the intratumor temperature reached 42° C., the mouse was injected with 150 µl LUV sample via the tail vein. Heating continued for 30 min after injection of the liposomes. After heating, the mouse was immediately sacrificed and the tumors excised. Tumors were frozen and thawed twice. PBS was added to each tumor at a 3:1 (PBS: tumor volume) ratio. The tumors were ground in a Polytron tissue homogenizer. After homogenization, cell lysis buffer was added to the tumor homogenate at a 1:1 ratio. The homogenates were incubated overnight and vortexed. The extracts were centrifuged at 10 k×g for 2 hr to remove undissolved cell matter. Samples were assayed by fluorometer as described in Example 4.

Figure 9:
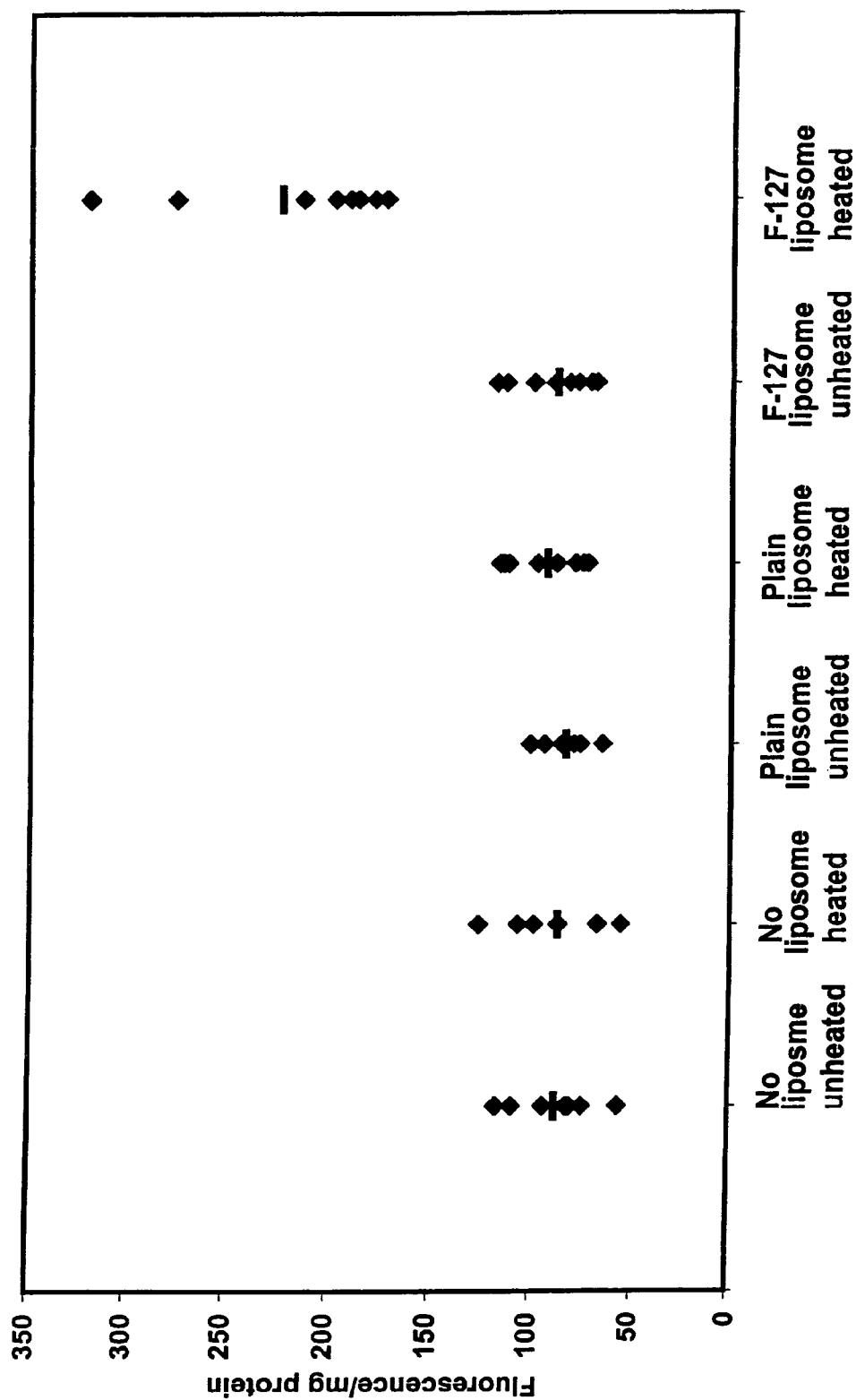
FIG. 9 is a representation of the association of released LY with tumors. Data is shown for 6 animals. The bars represent the mean value for each group.

To ensure that the increase of LY in the heated tumors is not due to heating effects on tissues, nor to the release of content due to no-specific heat-related leakage of liposomes containing no F127 (plain liposomes), two groups of control mice were used. Mice in one control group were injected with the same volume of PBS alone and those in the other control group were injected with LY-containing liposomes but no F127. The tumors on one leg of these control groups of mice were similarly heated, whereas the tumors on the other leg were unheated. Six mice in each control group and eight mice in the experimental group were used in two repeated experiments. FIG. 9 shows the fluorescence intensity per mg of tumor protein in these samples. All control samples showed an averaged background fluorescence level of 85–95, whereas the averaged fluorescence level for the heated tumors injected with LY/F127 is 221. A t-test was conducted between each control group and the experimental group. The p-value is <0.00002.

The data presented herein demonstrates that the composition and the method of the present invention can be used for temperature controlled content release from liposomes. Modifications obvious to one skilled in the art are intended to be included within the scope of the present invention as described by the specification and the claims.

REFERENCES

[1] Lasic, (Ed.), Liposomes: From physics to applications, Elsevier, Amsterdam, 1993.

[2] M. C. Woodle, D. D. Lasic, Sterically stabilized liposomes [Review], Biochim. Biophys. Acta 1113(2) (1992) 171–199.

[3] G. Blume, G. Cevc, Molecular mechanism of the lipid vesicle longevity in vivo, Biochim. Biophys. Acta 1146(2) (1993) 157–168.

[4] R. M. Straubinger, N. Duzgunes, D. Papahadjoupoulos, pH-sensitive liposomes mediate cytoplasmic delivery of encapsulated macromolecules, FEBS Lett. 179(1) (1985) 148–154.

[5] J. Connor, L. Huang, Efficient cytoplasmic delivery of a fluorescent dye by pH-sensitive immunoliposomes, J. Cell Biol. 101(2) (1985) 582–589.

[6] J. N. Weinstein, R. L. Magin, M. B. Yatvin, D. S. Zaharko, Liposomes and local hyperthermia: selective delivery of methotrexate to heated tumors, Science 204 (1979) 188–191.

[7] J-C. Kim, S. K. Bae, J-D. Kim, Temperature sensitivity of liposomal lipid bilayers mixed with poly(N-Isopropylacrylamide-co-acrylic acid), J. Biochem. 121 (1997)15–19.

[8] K. Kono, R. Nakai, K. Morimoto, T. Takagishi, Thermosensitive polymer-modified liposomes that release contents around physiological temperature, Biochim. Biophys. Acta 1416 (1999) 239–250.

[9] G. R. Anyarambhatla, D. Needham, Enhancement of the phase transition permeability of DPPC liposomes by incorporation of MPPC: a new temperature-sensitive liposome for use with mild hyperthermia, Journal of Liposome Research 9(4) (1999) 491–506.

[10] M. B. Yatvin, W. Kreutz, B. A. Horwitz, M. Shinitzky, pH-sensitive liposomes: possible clinical implications, Science 210 (1980) 1253–1255.

[11] M. Maeda, A. Kumano, D. A. Tirrell, $H^+$-induced release of contents of phosphatidylcholine vesicles bearing surface bound polyelectrolyte chains, J. Am. Chem. Soc. 110 (1988) 7455–7459.

[12] M. Zignani, D. C. Drummond, O. Meyer, K. Hong, J-C. Leroux, In vitro characterization of a novel polymeric-based pH-sensitive liposome system, Biochim. Biophys. Acta 1463(2) (2000) 383–394.

[13] C. Pidgeon, C. A. Hunt, Light sensitive liposomes, Photochem. Photobiol. 37(5) (1983) 491–494.

[14] V. C. Anderson, D. H. Thompson, Triggered release of hydrophilic agents from plasmalogen liposomes using visible light or acid, Biochim. Biophys. Acta 1109(1) (1992) 33–42.

[15] H. Hayashi, K. Kono, T. Takagishi, Temperature-dependent associating property of liposomes modified with a thermosensitive polymer, Bioconjugate Chem. 9(3) (1998) 382–389.

[16] M. Jamshaid, S. J. Farr, P. Kearney, I. W. Kellaway, Poloxamer sorption on liposomes: comparison with polystyrene latex and influence on solute efflux, Int. J. Pharm. 48 (1988) 125–131.

[17] M. C. Woodle, M. S. Newman, F. J. Martin, Liposome leakage and blood circulation: comparison of adsorbed block copolymers with covalent attachment of PEG, Int. J. Pharm. 88 (1992) 327–334.

[18] P. Alexandridis, Poly(Ethylene Oxide) Poly(Propylene Oxide) block copolymer surfactants [Review], Curr. Op. Colloid Int. Sci. 2(5) (1997) 478–489.

[19] P. Alexandridis, T. A. Hatton, in: V. Pillai, D. O. Shah (Eds.), Dynamic properties of interfaces and association structures, Chapter 12, AOCS Press, Champaign, Ill., 1996, pp. 231–262.

[20] P. Alexandridis, J F. Holzwarth, T A. Hatton, Micellization Of Poly(Ethylene Oxide)-Poly(Propylene Oxide)-Poly(Ethylene Oxide) triblock co-polymers in aqueous solutions—thermodynamics of copolymer association, Macromolecules 27(9) (1994) 2414–2425.

[21] J. N. Weinstein, S. Yoshikami, P. Henkart, R. Blumenthal, W. A. Hagins, Liposome-cell interaction: transfer and intracellular release of a trapped fluorescent marker, Science 195(4277) (1977) 489–492.

[22] K-H. Cheng, T. Wiedmer, P. J. Sims, Fluorescence resonance energy transfer study of the associative state of membrane-bound complexes of complement proteins C5b-8, J. Immunol. 135(1) 1985 459–464.

[23] H. Du, P. Chandaroy, S. W. Hui, Grafted poly-(ethylene glycol) on lipid surfaces inhibits protein adsorption and cell adhesion, Biochim. Biophys. Acta 1326(2) (1997) 236–248.

[24] M. S. Webb, T. O. Harasym, D. Masin, M. B. Bally, L. D. Mayer, Sphingomyelin-cholesterol liposomes significantly enhance the pharmacikinetic and therapeutic properties of vincristine in murine and human tumor models, Br. J. Cancer 72(4) (1995) 896–904.

[25] I. Ogihara-Umeda, S. Kojima, Cholesterol enhances the delivery of liposome-encapsulated gallium-67 to tumors, Eur. J. Nucl. Med. 15(9) (1989) 612–617.

[26] C. Kirby, J. Clarke, G. Gregoriadis, Effect of cholesterol content of small unilamellar liposomes on their stability in vivo and in vitro, Biochem. J. 186 (1980) 591–598.

[27] M. H. Gaber, K. Hong, S. K. Huang, D. Papahadjoupoulos, Thermosensitive sterically stabilized liposomes: formulation and in vitro studies on mechanisms of doxorubicin release by bovine serum and human plasma. Pharm. Res. 12 (1995) 1407–16.

[28] P. Alexandridis and J F. Holzwarth, Differential scanning calorimetry investigation of the effect of salts on aqueous solution properties of an amphiphilic block copolymer (poloxamer). Langmuir, 13, 6074–6082, 1997

What is claimed is:

1. A composition for temperature controlled release of one or more delivery agents comprising large unilamellar vesicles (LUVs) encapsulating the delivery agents and poloxamer molecules, wherein the concentration of the poloxamer in the composition is between 0.01% w/v to 0.2% w/v, wherein the critical micellar temperature (CMT) of the poloxamer at a concentration between 0.01% to 0.2% is between 33° C. and 43° C. and wherein above the CMT, the poloxamer molecules become incorporated into the lipid bilayer membrane of the LUVs making the LUVs leaky thereby effecting release of the one or more delivery agents from the LUVs.

2. The composition of claim 1, wherein the poloxamer is Pluronic 127.

3. The composition of claim 1, wherein the critical micellar temperature is about 37° C.

4. The composition of claim 1, wherein the agent is a therapeutic agent.

5. The composition of claim 1, wherein the agent is a diagnostic agent.

6. The composition of claim 1, wherein the LUV is made with di-oleoyl phospatidylcholine and cholesterol mixed in a 1:1 ratio.

7. The composition of claim 1, wherein the polaxamer is selected from the group consisting of Pluronic F87, Pluronic F88, Pluronic F98, Pluronic F108, and Pluronic P188.

8. The composition of claim 1, wherein the LUV comprises phopholipids selected from the group consisting of phosphatidylcholine, phosphatidylserine, phosphatidylglycerol, phosphatidylethanolamine, phosphatidylinositol and combinations thereof.

9. The composition of claim 8 wherein the LUV further comprises sphingolipids, glycolipids, fatty acids and cholesterol.

10. A method of delivering one or more delivery agents to a target site in an individual comprising the steps of:
   a) providing large unilamellar vesicles (LUVs) encapsulating one or more delivery agents and poloxamer molecules, wherein the concentration of the poloxamer in the composition is between 0.01% w/v to 0.2% w/v, wherein the critical micellar temperature (CMT) of the poloxamer at a concentration between 0.01% to 0.2% is between 33° C. and 43° C. and wherein above the CMT, the poloxamer molecules become incorporated into the lipid bilayer membrane of the LUVs making the LUVs leaky thereby effecting release of the one or more delivery agents from the LUVs;
   b) administering the LUVs to the individual; and
   c) increasing the temperature of the target site to above the CMT effecting release of the one or more delivery agents from the LUVs.

11. The method of claim 10, wherein the wherein the poloxamer is Pluronic 127.

12. The method of claim 10, wherein the poloxamer is selected from the group consisting of Pluronic F87, Pluronic F88, Pluronic F98, Pluronic F108, and Pluronic P188.

13. The method of claim 10, wherein the critical micellar temperature of the poloxamer is about 37° C.

14. The method of claim 10, wherein the agent is a therapeutic agent.

15. The method of claim 10, wherein the agent is a diagnostic agent.

16. The method of claim 10, wherein the LUV is made with di-oleoyl phospatidylcholine and cholesterol mixed in a 1:1 ratio.

17. The method of claim 10, wherein the target site is a tumor.

18. A method of inhibiting the growth of a tumor in an individual comprising the steps of:
   a) administering to the individual a liposomal composition comprising large unilamellar vesicles (LUVs) encapsulating one or more anti-tumor agents and poloxamer molecules, wherein the concentration of the poloxamer in the composition is between 0.01% w/v to 0.2% w/v, wherein the critical micellar temperature (CMT) of the poloxamer at a concentration between 0.01% to 0.2% is between 33° C. and 43° C. and wherein above the CMT, the poloxamer molecules become incorporated into the lipid bilayer membrane of the LUVs making the LUVs leaky thereby effecting release of the one or more anti-tumor agents from the LUVs; and
   b) and applying heat to raise the temperature at, within or near the tumor to above the CMT thereby effecting release of the one or more anti-tumor agents at, within or near the tumor.

19. The method of claim 18, wherein the poloxamer is Pluronic 127.

20. The method of claim 18, wherein the critical micellar temperature is about 37° C.

21. The method of claim 18, wherein the agent is a therapeutic agent.

22. The method of claim 18, wherein the agent is a diagnostic agent.

23. The method of of claim 18, wherein the LUV is made with di-oleoyl phospatidylcholine and cholesterol mixed in a 1:1 ratio.

24. The composition of claim 1, wherein the delivery agent is water soluble.

25. The method of claim 10, wherein the delivery agent is water soluble.

26. The method of claim 18, wherein the anti-tumor agent is water soluble.

* * * * *

UNITED STATES PATENT AND TRADEMARK OFFICE
CERTIFICATE OF CORRECTION

PATENT NO. : 6,964,778 B1  Page 1 of 1
DATED : November 15, 2005
INVENTOR(S) : Hui et al.

It is certified that error appears in the above-identified patent and that said Letters Patent is hereby corrected as shown below:

Column 16,
Line 23, delete "and".

Signed and Sealed this

Seventh Day of March, 2006

JON W. DUDAS
*Director of the United States Patent and Trademark Office*